United States Patent
Áwengen et al.

(10) Patent No.: US 9,895,252 B2
(45) Date of Patent: Feb. 20, 2018

(54) SEPTAL IMPLANT (71) Applicant: HEINZ KURZ GMBH MEDIZINTECHNIK, Dusslingen (DE)

(72) Inventors: Daniel Felix Áwengen, Bottmingen (CH); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 569 days.

(21) Appl. No.: 13/955,321

(22) Filed: Jul. 31, 2013

(65) Prior Publication Data

US 2014/0039619 A1    Feb. 6, 2014

(30) Foreign Application Priority Data

Aug. 3, 2012   (DE) .................. 10 2012 107 123

(51) Int. Cl.
*A61F 5/08* (2006.01)
*A61F 2/18* (2006.01)

(52) U.S. Cl.
CPC ............. *A61F 5/08* (2013.01); *A61F 2/186* (2013.01)

(58) Field of Classification Search
CPC .................................. A61F 5/08; A61F 2/186
USPC .............. 623/10, 17.18, 14.12; 606/204.45
See application file for complete search history.

(56) References Cited

U.S. PATENT DOCUMENTS

| | | | | |
|---|---|---|---|---|
| 4,592,357 A * | 6/1986 | Ersek | | 606/199 |
| 5,094,233 A | 3/1992 | Brennan | | |
| 5,931,799 A * | 8/1999 | Guastella et al. | | 602/6 |
| 6,322,590 B1 | 11/2001 | Sellers et al. | | |
| 7,695,501 B2 * | 4/2010 | Ellis et al. | | 606/281 |
| 7,972,379 B2 | 7/2011 | Jung et al. | | |
| 2007/0270899 A1* | 11/2007 | aWengen et al. | | 606/199 |
| 2011/0251634 A1* | 10/2011 | Gonzales et al. | | 606/199 |
| 2012/0078367 A1 | 3/2012 | Hristov et al. | | |

(Continued)

FOREIGN PATENT DOCUMENTS

| | | |
|---|---|---|
| EP | 1 475 056 | 11/2004 |
| WO | 00/06327 | 2/2000 |

(Continued)

OTHER PUBLICATIONS

"Mapping thickness of nasal septal catilage" Hwang, K. Jan. 21, 2010.*

(Continued)

*Primary Examiner* — Thomas J Sweet
*Assistant Examiner* — Daniel Bissing
(74) *Attorney, Agent, or Firm* — Collard & Roe, P.C.

(57) ABSTRACT

A rhinological implant for straightening the nasal septum is fastened on both sides of a septum (S), separating left and right sides of a nasal cavity of a human nose, on the outer surface of the septum (S), in the left and the right sides of the nasal cavity. Before implantation, the implant is folded up from an initially flat blank into an implantable three-dimensional shape. The implant has a central back section which in an implanted state wraps around the free lower edge of the septum. Two side sections are provided on either side of the central back section to extend symmetrically with respect to the central back section. In the implanted state, the two side sections bear via the entire surface against the two diametrically opposed outer surfaces of the septum (S).

19 Claims, 11 Drawing Sheets

(56) References Cited

U.S. PATENT DOCUMENTS

2013/0006293 A1* 1/2013 Smith .......................... 606/199

FOREIGN PATENT DOCUMENTS

| WO | 2008/153263 | 12/2008 |
| WO | 2010/059586 | 5/2010 |

OTHER PUBLICATIONS

Jul. 26, 2012 Internet page Reuter Type Intranasal Splints http://www.bess.de/rhinologie/septumschienen/septumschiene-nach-reuter.html.
Boenisch, M., et al: "Septum Reconstruction With PDS Implant" HNO 1999, June, 47 (6) English Abstract.

* cited by examiner

SEPTAL IMPLANT

CROSS-REFERENCE TO A RELATED APPLICATION

The invention described and claimed hereinbelow is also described in German Patent Application DE 10 2012 107 123.3, filed on Aug. 3, 2012. The German Patent Application, subject matter of which is incorporated herein by reference, provides the basis for a claim of priority of invention under 35 U.S.C. 119(a)-(d).

BACKGROUND OF THE INVENTION

The invention relates to a rhinological implant for straightening the nasal septum, which can be fastened on both sides of the septum of the human nose on the outer surface of the septum in each case in the left and right sides of the nasal cavity. Before implantation, the implant is folded up from an initially flat blank into the subsequent implantable, three-dimensional shape thereof.

Such an implant for straightening the septum is known to be available from Bess Medizintechnik GmbH, headquartered in Berlin, Germany, from 26 Jul. 2012.

A method of implanting such an implant (i.e., a tissue piece or substance that is usually exogenous), into the human body is known for a long time in medical technology and is carried out in many variations to eliminate functional defects of various body parts and/or psychic impairments.

It also is known that the cartilaginous portion of the human nose comprises the nasal septum, the triangular cartilage, and the alar cartilage.

In functional and cosmetic nasal surgery, the objective in many cases is to straighten the septum in order to improve the air flow within the nasal passage or, to simply improve the appearance of the nose. Such known procedures also typically include changing other structures.

Presently, different suturing or cartilage transplant techniques are used to straighten the septum. In the following, the differences between septoplasty and the collumellar strut technique will be discussed.

In greater detail, the sole objective of septoplasty is to straighten the septum and, therefor, optimize the air inflow through the nose. This surgery is purely functional. A variety of surgical techniques is used therefor, which utilize sutures and transplants to achieve the objective.

The straightening of a deviated septum can be one of the greatest challenges in rhinoplasty. Various methods, which depend substantially on the experience and expertise of the operating surgeon, may be used for this purpose.

Disarticulation techniques, up to and including specific cartilage incisions, can play a greater or lesser role. Straightening the septum specifically in the central arch is a difficult undertaking and is hardly a simple operation.

In contrast to a straightening of the septum, the objective of the collumellar strut technique is to raise the tip of the nose for cosmetic reasons. In the collumellar strut technique, a strut is slid between the two ends of the two alar cartilages in order to raise the tip of the nose. The graft/implant is placed into a pocket between the medial crura of the alar cartilages over the Spina nasalis anterior and is fastened between the medial crura using sutures extending therethrough.

This technique is described in US 2012/0078367 A1, for example. The implant discussed therein is biodegradable and, therefore, is not intended to remain in place for a long period of time. The target region is the lower third of the nose, mainly the region around the nasal tip. This technique also involves connecting the implant to the septum but not straightening the septum. Instead, the technique involves extending the septum if the septum has been shortened due to an external influence or, is short from a cosmetic perspective. The curved parts of the above-described implant do not exceed 20 mm in length in the longitudinal extension thereof. When placed onto the base of the Spina nasalis, the curved parts extend just to the end of the septum and accommodate the two crura of the alar cartilages. Therefore, the septum is never straightened. In the seat of the implant in the implanted state would be entirely unsuitable for septum straightening.

Document WO 2008/153263 A1 describes techniques that are designed to raise the nasal tip, where the septum also is discussed in that case. In the technique described therein, the implant must be placed at the upper edge of the septum cartilage. In that case, the objective is to stabilize the nasal tip implant.

Known implant systems according to US 2012/0078367 A1 and, WO 2008/153263 A1, are known to disclose techniques which attempt to utilize the end of the septum for stabilization or extension. However, neither of the two systems is designed or suitable for permanently straightening the septum.

In order to straighten the septum, it is known to apply techniques using PDS plates (e.g. described in: HNO.1999 June; 47 (6):546-50), which are cut to fit and are sutured onto the septum. The extremely thin plate implants resorb after 10 to 25 weeks, leaving substantially no residue.

Also known are Reuter-type intranasal splints made of silicone that are known to be available from Bess Medizintechnik GmbH, headquartered in Berlin, Germany Reuter-type intranasal splints are more stable implants for straightening the septum. These implants are used for the splinting of the nasal septum and to minimize the risk of adhesion between the septum and the lateral nasal wall. Reuter-type intranasal splints are designed with a slit for smoother insertion and removal and comprise pre-punched holes for suture fixation. The material from which Reuter-type intranasal splints are made is said to be fluoroplastic. However, the splints must be removed from the nose after a few weeks since silicone is not stable over the long term and potentially leads to infections.

SUMMARY OF THE INVENTION

The present invention overcomes the shortcomings of known arts, such as those mentioned above.

To that end, the present invention modifies Reuter-type intranasal splints using simple technical means in such a way that prevents the disadvantages and, after surgery, the implant permanently bears against the nasal septum as closely as possible.

The invention solves the problem in a manner that is surprisingly simple and cost-effective in that the implant has a central back section, which is flat or curved upward very slightly from a horizontal plane, angled at a splaying angle ($\omega$)>100°) preferably splaying angle ($\omega$)>160°), or has the shape of a barrel having a radius of curvature (r)≥0.5 mm from the horizontal plane and. In the implanted state, the inventive implant wraps around the free lower edge of the septum and two side sections of the implant are provided on either side of the central back section. The two side sections extend symmetrically with respect to the central back section, angled upwardly at an angle ($\varphi$) of approximately 90° in each case relative to the central back section, and, in the implanted state, bear via the entire surface thereof against the two diametrically opposed outer surfaces of the septum.

The invention provides for straightening the septum using a structure that is specially formed and, therefore, permanently mechanically stable. The implant is geometrically designed such that the entire region of the septum is covered. This is achieved in that the implant wraps around the free lower edge of the septum. Furthermore, both sides of the implant are perforated such that the implant can be easily and securely fixed on both sides of the septum. The thickness and the related stiffness of the implant are important insofar as, over the long-term, the septum cartilage should adapt to the shape of the implant and not vice-versa.

Therefore, a particularly good geometric adaptation of the implant to the (normal) configuration of the human septum and particularly good placement of the implant against the outer surfaces thereof are achieved without increasing the complexity of production. In particular, hollow spaces do not form between the implant and the septum after surgery. That is, hollow spaces do not form in the region of the central back section or at the side sections adjoining the central back section on both sides. Instead, the implant bears, via the entire surface thereof facing the septum, closely against the septum, which also induces a particularly good mechanical hold of the implant on the septum.

In an embodiment, each of the two side sections of the implant has a first subsection, which directly adjoins the central back section, and extends substantially parallel thereto. Each of the two side sections has a second subsection toward the free ends thereof, wherein the second subsections adjoin the respective first subsection and extend at an angle relative thereto. These simple measures greatly increase the long-term mechanical stability of the implant. In addition, the flat, fixed seat of the implant against the two lateral surfaces of the nasal septum is further improved.

The implant can have several different shapes. In an embodiment, the implant has an angular contour, in particular being bent in the plane in the shape of a V. Preferably and, advantageously, the tip of the "V" should be slightly rounded in order to prevent injury. The implant, therefore, has a boomerang-shaped contour.

The implant may be formed with a trapezoidal shape and/or comprise more complicated structures having branches, which can contribute to stabilization after the implant is bent into the final three-dimensional shape thereof. In embodiments, the bending-off angles of the free ends of the two side sections are designed such that, in the implanted state, the side sections are in close spatial contact with the septum. Preferably, the side sections symmetrically clamp the septum on both sides under load, thereby contributing to a particularly good and permanent seat of the implant.

It is preferable that the side sections have rounded corners, thereby reliably preventing anything from becoming stuck or even gored during implantation, and also to rule out the possibility of injury in the implanted state.

In embodiments, the back section is formed of segments of as network structure in order to increase the flexibility of the implant in this region via extensibility and compressibility.

In addition or alternatively thereto, segments of a network structure also can be incorporated into the side sections, thereby further increasing the two-dimensional flexibility.

Embodiments of the inventive implant also may display one or more spikes incorporated into the side sections. The spikes dig into the septum cartilage upon implantation And thereby provide an excellent and extremely long-term hold of the implant.

Alternatively, or additionally, the inventive implant comprises perforations. The weight of the implant is thereby reduced, and the portion of exogenous material introduced into the human body via the implant is reduced to the greatest extent possible. The perforations also promote the fusion of the implant with the tissue.

The perforations are preferably present on the side sections of the implant and on the back section located therebetween. The perforations are formed as circular holes or elongated holes, for example. The perforations also are used for secure fixation on the triangular cartilage by means of suturing.

Establishing a fastening of the implant that is stable for the long term via suturing on the cartilage, however, usually takes a great deal of time and is often somewhat complicated due to the spatial conditions.

In an embodiment, a connecting element is therefore provided, which, in the implanted state of the implant, extends through the entire septum and interconnects the two side sections, which are diametrically opposed with respect to the septum. The connecting element is preferably a rivet element for permanently and securely fastening via an easily created perforation through the septum. This type of fastening also can be freely combined with the other fastening types described above, in order to ensure a particularly secure seat of the implant on the septum.

Metals and the alloys thereof are predestined for use as the material for surgical and orthopedic implants designed to remain in the body permanently, as they tend to display very good biocompatibility as well as a high endurance limit and elasticity. Despite having a relatively small thickness, implants made of materials such as titanium or titanium compounds have excellent mechanical properties having a long useful life. Stainless steel is also well-suited for the aforementioned purposes. Although the inventive implant also can be made of a suitable plastic, the inventive implant is preferably made of metal, in particular, titanium, a titanium alloy or stainless steel.

Embodiments are preferred in which the implant is made of a material having a memory effect and/or superelastic properties, preferably Nitinol. Forming the implants of material having a memory effect and/or superelastic properties makes it possible to provide the implant with optimal spring properties relative to the septum, e.g., by subjecting the implant to a suitable thermal treatment.

In addition to the good biocompatibility of the material itself that is used, the implant also may comprise a special biocompatible and/or disinfectant coating.

In order to obtain a finely tuned shape of the implant, the implant can be advantageously formed or manufactured using laser technology.

In a further embodiment, the implant is manufactured using injection molding according to the micro injection-moldin (MIM) process, which is known, per se, from WO 00/06327 A2. Such MIM process renders it possible to achieve extremely cost favorable production of very large item counts as well with a consistent dimensional tolerance. This is distinguished from conventional implants, which are usually handmade (in the manner of jewelry) and, are therefore relatively expensive to manufacture and can vary individually in terms of dimensional tolerance.

BRIEF DESCRIPTION OF THE DRAWINGS

Further features and advantages of the invention will become apparent from the description of embodiments that follows, with reference to the attached figures, wherein:

FIG. 1b presents a schematic perspective view of an alternative embodiment of the implant depicted in FIG. 1a;

FIG. 1c presents a schematic perspective view of an alternative embodiment of the implant depicted in FIG. 1a;

FIG. 1d presents a schematic perspective view of an alternative embodiment of the implant depicted in FIG. 1a;

FIG. 1e presents a schematic perspective view of an alternative embodiment of the implant depicted in FIG. 1a;

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

The inventive rhinological implants for straightening the nasal septum $1a$; $1b$; $1c$; $1d$; $1e$; $2a$; $2b$; $2c$; $3a$; $3b$; $4a$, as shown in the figures can be fastened on both sides of the septum S of the human nose, on the outer surface of the septum S in each case in the left and right sides of the nasal cavity. Before implantation, the implant ($1a$; $1b$; $1c$; $1d$; $1e$; $2a$; $2b$; $2c$; $3a$; $3b$; $4a$) is folded up from an initially flat blank into the subsequent, implantable three-dimensional shape thereof.

The implant $1a$; $1b$; $1c$; $1d$; $1e$; $2a$; $2b$; $2c$; $3a$; $3b$; $4a$ has a central back section $11a$; $11b$; $11c$; $11d$; $11e$; $21a$; $21b$; $21c$; $31a$; $31b$; $41a$, which is flat or curved upward very slightly from a horizontal plane, angled at a splaying angle $\omega > 100°$, preferably $\omega > 160°$. Alternatively, the central back section has the shape of a barrel having a radius of curvature of $r \geq 0.5$ mm from the horizontal plane and, in the implanted state, wraps around the free lower edge of the septum.

Figure 3A:
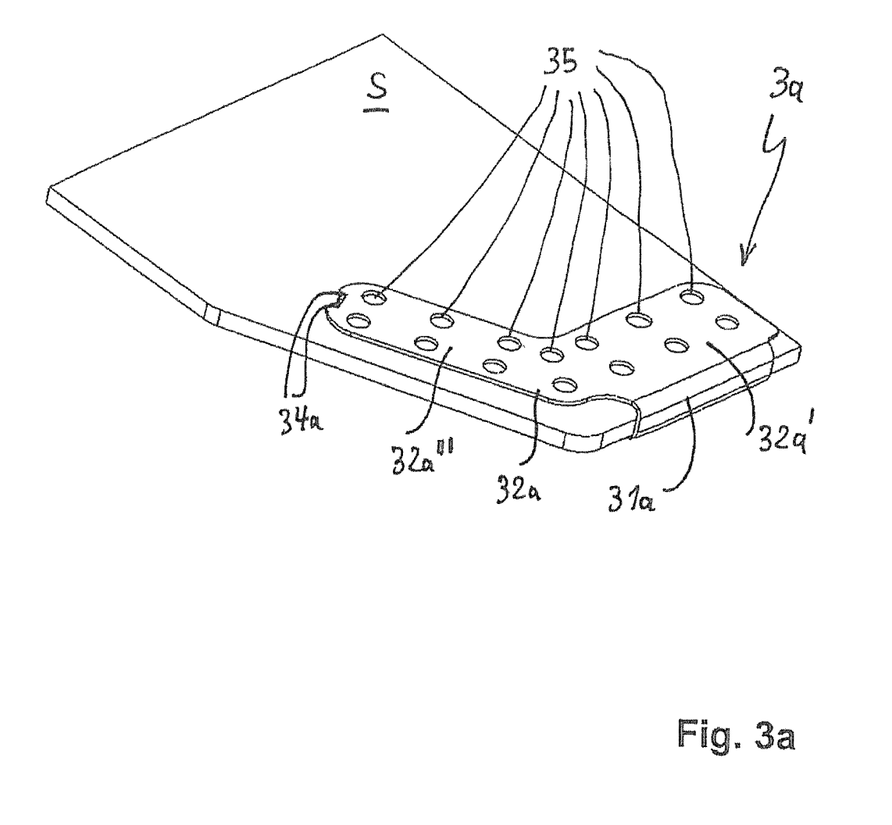
FIG. 3a presents a schematic perspective view of an implant having a back section between two longitudinal sides of two side sections in the implanted state on the schematically indicated septum cartilage, where spikes engage into the cartilage at the free ends of the second subsections of each of the two side sections.
Figure 3B:
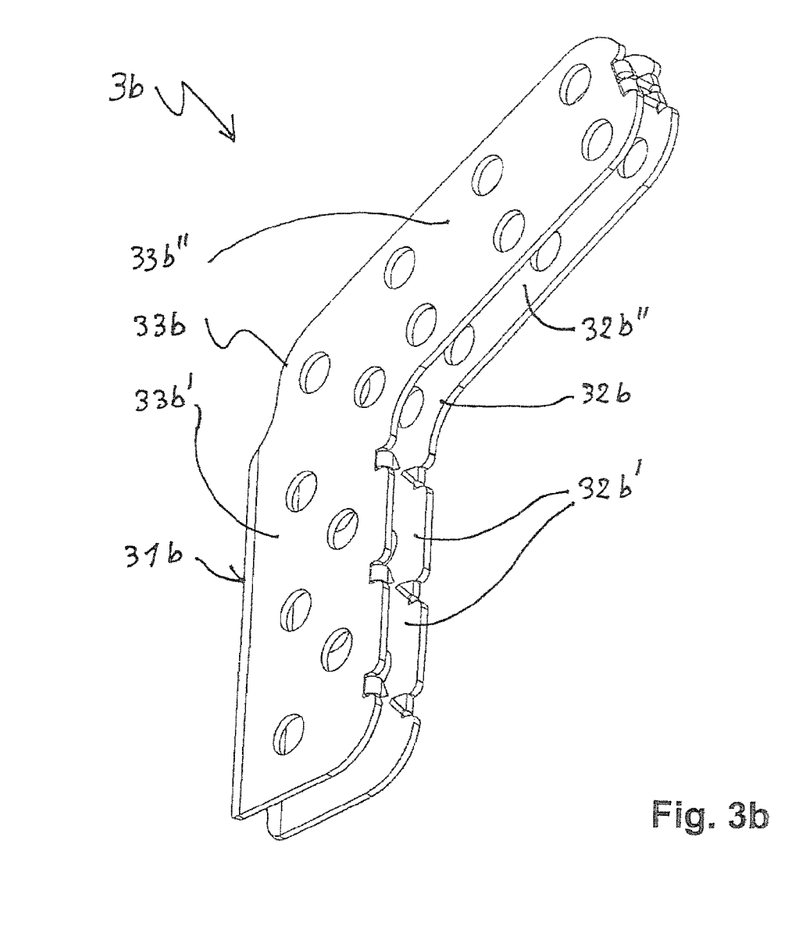
FIG. 3b depicts the implant of FIG. 3a without the septum cartilage and with additional spikes at the free edges of the two side sections facing away from the back section.
Figure 3C:
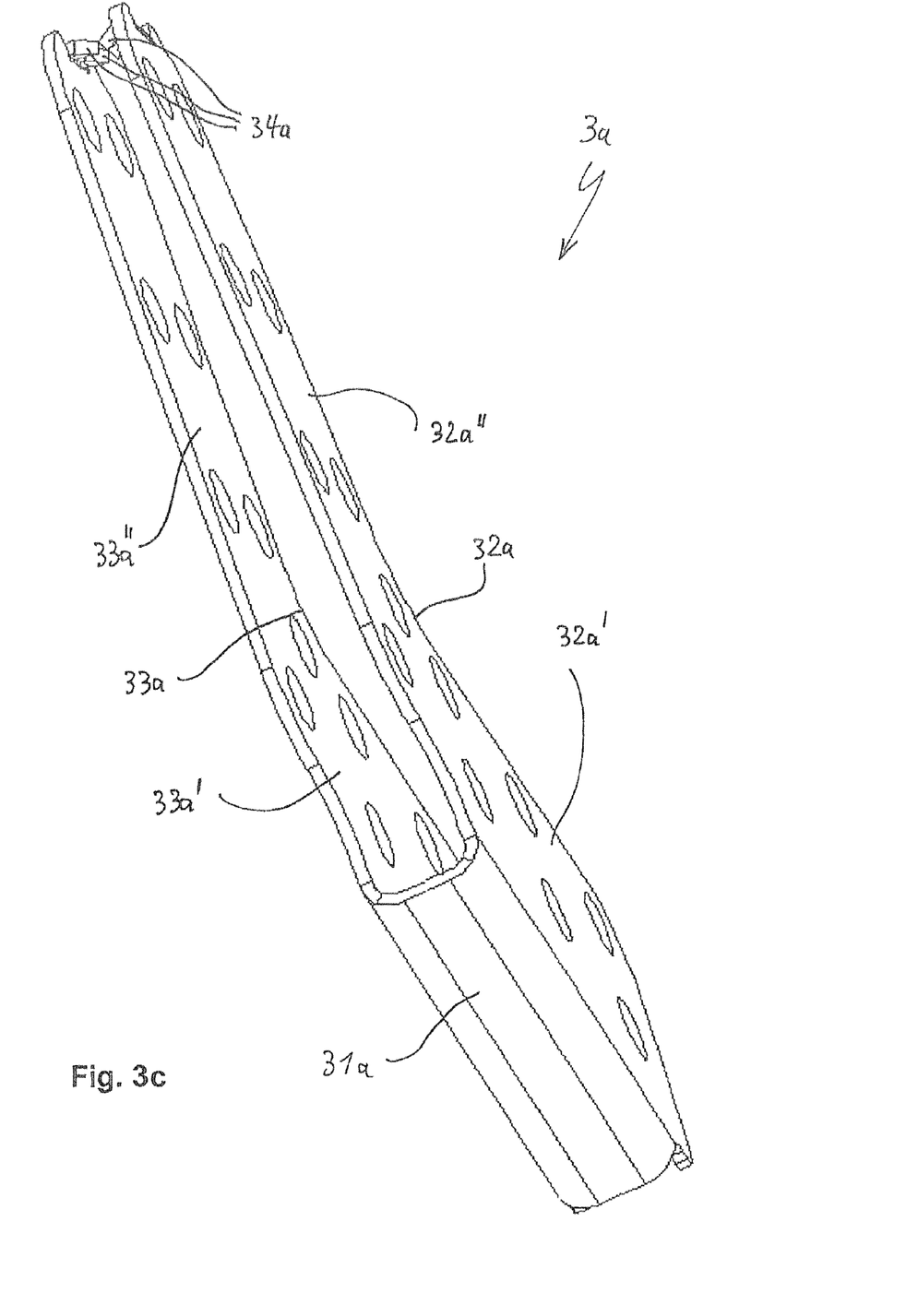
FIG. 3c depicts the implant of FIG. 3a without the septum cartilage depicted therein.
Figure 3D:
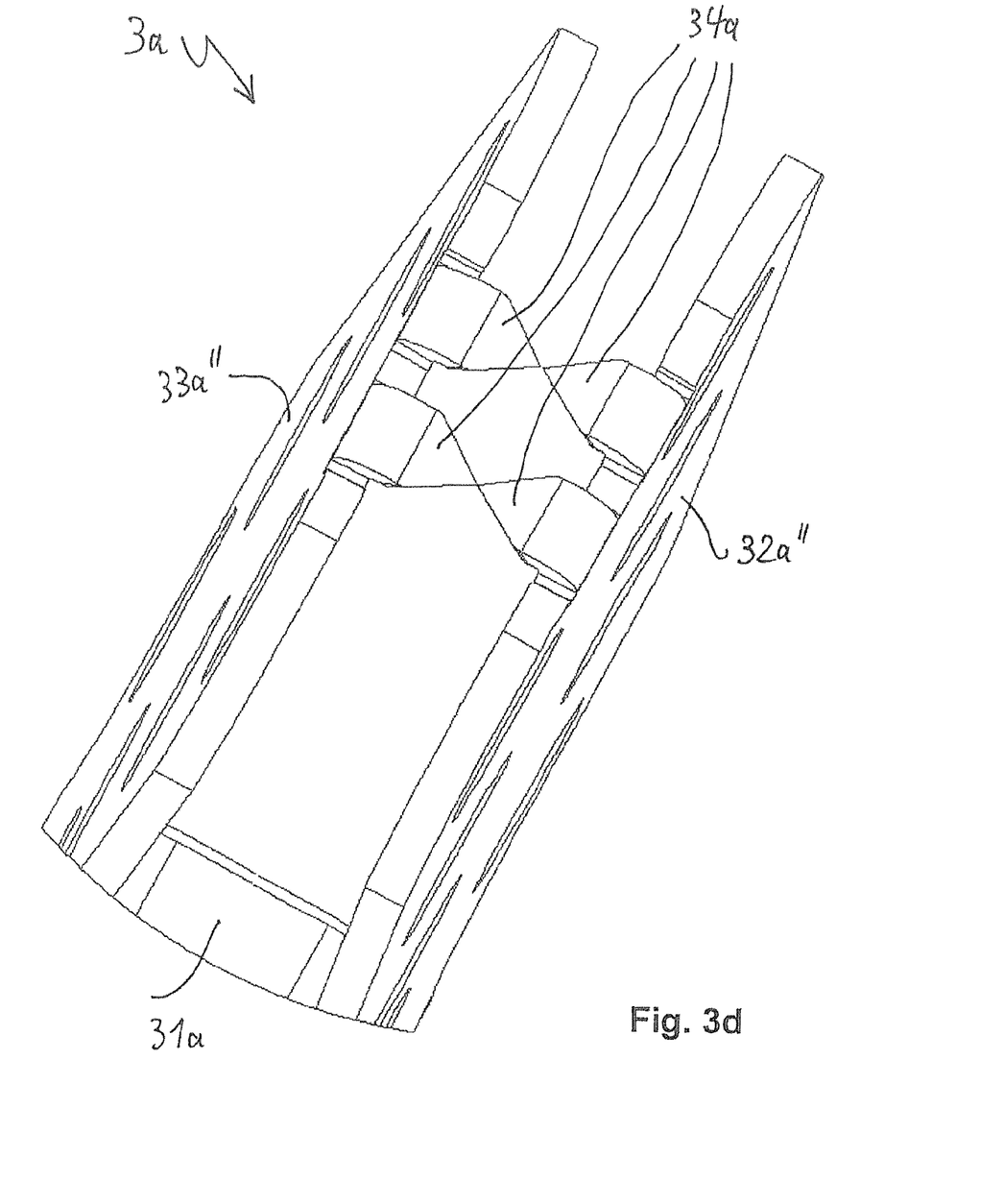
FIG. 3d presents and enlarged view of the region of the spikes depicted in FIG. 3c.

Two side sections $12a$, $13a$; $12b$, $13b$; $12c$, $13c$: $12d$, $13d$; $12e$, $13e$; $22a$, $23a$; $22b$, $23b$; $22c$, $23c$; $32a$, $33a$; $32b$, $33b$; $42a$, $43a$ are provided on either side of the central back section $11a$; $11b$; $11c$; $11d$; $11e$; $21a$; $21b$; $21c$; $31a$; $31b$; $41a$. The two side sections extend symmetrically with respect to the central back section $11a$; $11b$; $11c$; $11d$; $11e$; $21a$; $21b$; $21c$; $31a$; $31b$; $41a$, are angled upwardly at an angle φ of approximately 90° in each case relative to the central back section $11a$; $11b$; $11c$; $11d$; $11e$; $21a$; $21b$; $21c$; $31a$; $31b$; $41a$, and, in the implanted state, bear via the entire surface thereof against the two diametrically opposed outer surfaces of the septum, as shown In FIG. 3a.

In all the embodiments depicted, the corners of the side sections $12a$, $13a$; $12b$, $13b$; $12c$, $13c$; $12d$, $13d$; $12e$, $13e$; $22a$, $23a$; $22b$, $23b$; $22c$, $23c$; $32a$, $33a$; $32b$, $33b$; $42a$, $43a$ are rounded.

FIGS. 1a-e show, in schematic perspective views, five embodiments (i.e., implants $1a$; $1b$; $1c$; $1d$; $1e$) of the inventive implant. In each case, the implant is formed by curving a flat strip into a roof-like, three-dimensional shape, which is not depicted separately in the drawing.

The implant embodiments $3a$; $3b$, depicted in FIGS. 3a-d, are identical to implants $1a$; $1b$; $1c$; $1d$; and $1e$, in that each of the two side sections $12a$, $13a$; $12b$, $13b$; $12c$, $13c$; $12d$, $13d$; $12e$, $13e$; $32a$, $33a$; $32b$, $33b$ has a first subsection $12a'$, $13a'$; $12b'$, $13b'$; $12c'$, $13c'$; $12d'$, $13d'$; $12e'$, $13e'$; $32a'$, $33a'$; $32b'$, $33b'$, which directly adjoins the central back section $11a$; $11b$; $11c$; $11d$; $11e$; $31a$; $31b$ and extends substantially parallel thereto. Also, each of the two side sections $12a$, $13a$; $12b$, $13b$; $12c$, $13c$; $12d$, $13d$; $12e$, $13e$; $32a$, $33a$; $32b$, $33b$ has a second subsection $12a''$, $12b''$, $13b''$; $12c''$, $13c''$; $12d''$, $13d''$; $12e''$, $13e'$; $32a''$, $33a''$; $32b''$, $33b''$ toward the free ends thereof. The second subsections adjoin the respective first subsection $12a'$, $13a'$; $12b'$, $13b'$; $12c'$, $13c'$; $12d'$, $13d'$; $12e'$, $13e'$; $32a'$, $33a'$; $32b'$, $33b'$ and extend at an angle relative thereto.

In particular, the implant $1a$; $1b$; $1c$; $1d$; $1e$; $3a$; $3b$ can have an angular contour, preferably a V-shaped or boomerang-shaped contour. As a result, the long-term mechanical stability of the implant is greatly increased and the flat, fixed seat against the two lateral surfaces of the nasal septum can be further improved.

In the implants $1d$; $1e$, shown in FIGS. 1d and 1e, the back section $11d$; $11e$ is formed of segments of a network structure. Segments of a network structure also can be incorporated into the side sections $12e$, $13e$, thereby greatly increasing the flexibility of the implant and providing a certain amount of variability in the adaptation to specific geometric conditions found in a particular patient.

As also shown in FIGS. 1a to 1e, the back section $11a$; $11b$; $11c$; $11d$; $11e$ of the implants $1a$; $1b$; $1c$; $1d$; $1e$, according to the invention, need not be completely flat. In some embodiments the back section also can be angled very slightly or have a very slight curvature without losing all the advantages of the invention. In contrast, in many people, the free lower edge of the septum S is also not entirely flat, but rather is very slightly arched making it possible to achieve a particularly good adaptation of the implant to the patient's individual anatomical details.

Figure 1A:
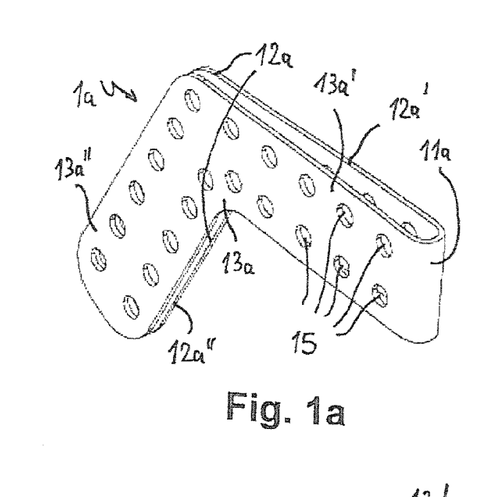
FIG. 1a presents a schematic perspective view of one embodiment of the implant according to the invention, which implant comprises a back section between two narrow sides of the two side sections.
Figure 1B:
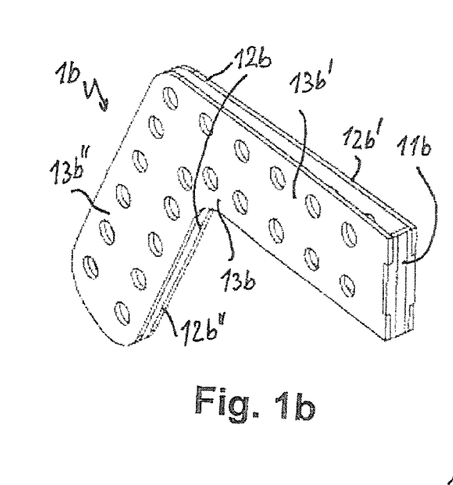
Figure 1C:
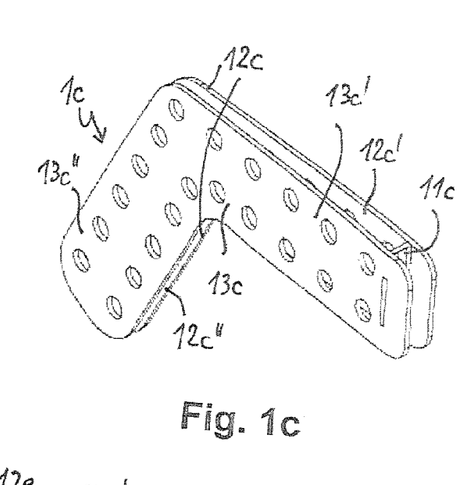
Figure 1D:
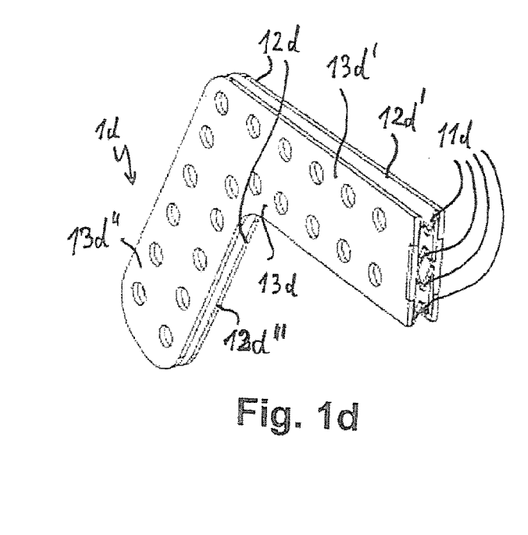
Figure 1E:
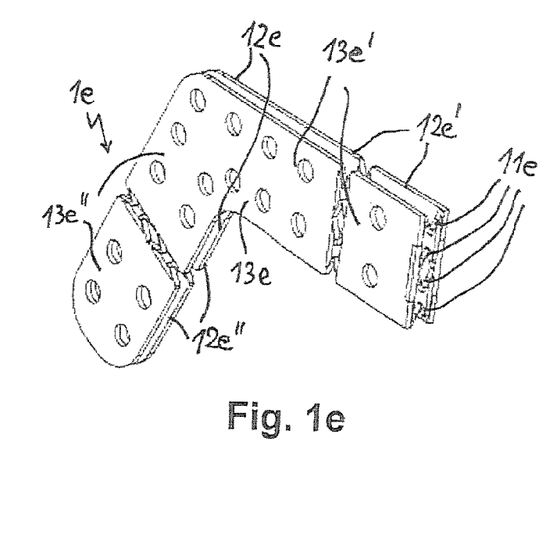
Figure 2A:
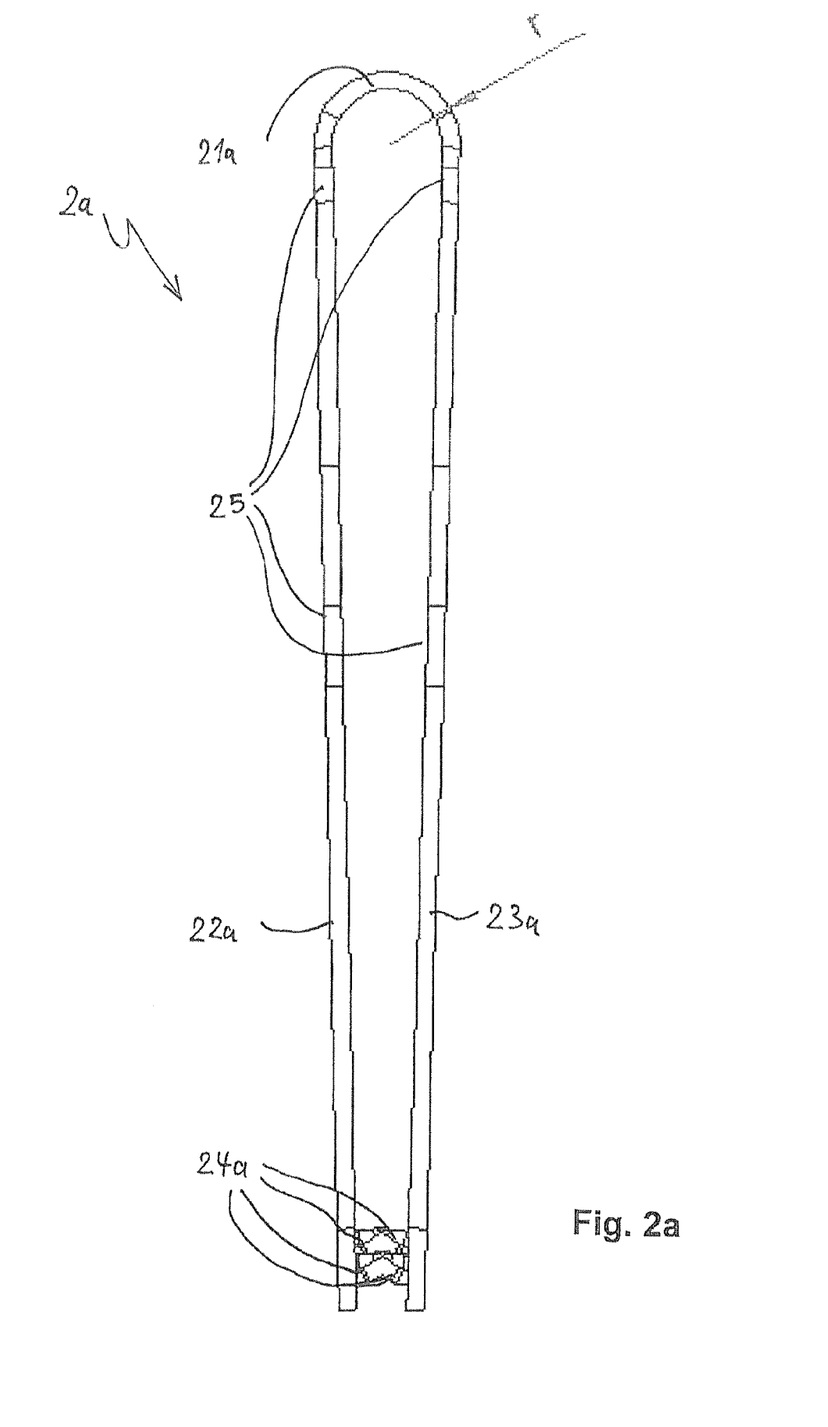
FIG. 2a is a schematic sectional drawing of the two side sections of the implant depicted in FIG. 1a, comprising a back section rounded with a radius of curvature r.

Therefore, FIG. 2a shows that implant 2a has a slight barrel-shaped curvature with a relatively great radius of curvature r≥0.5 mm and, therefore wraps around the free lower edge of the septum in the implanted state.

Figure 2B:
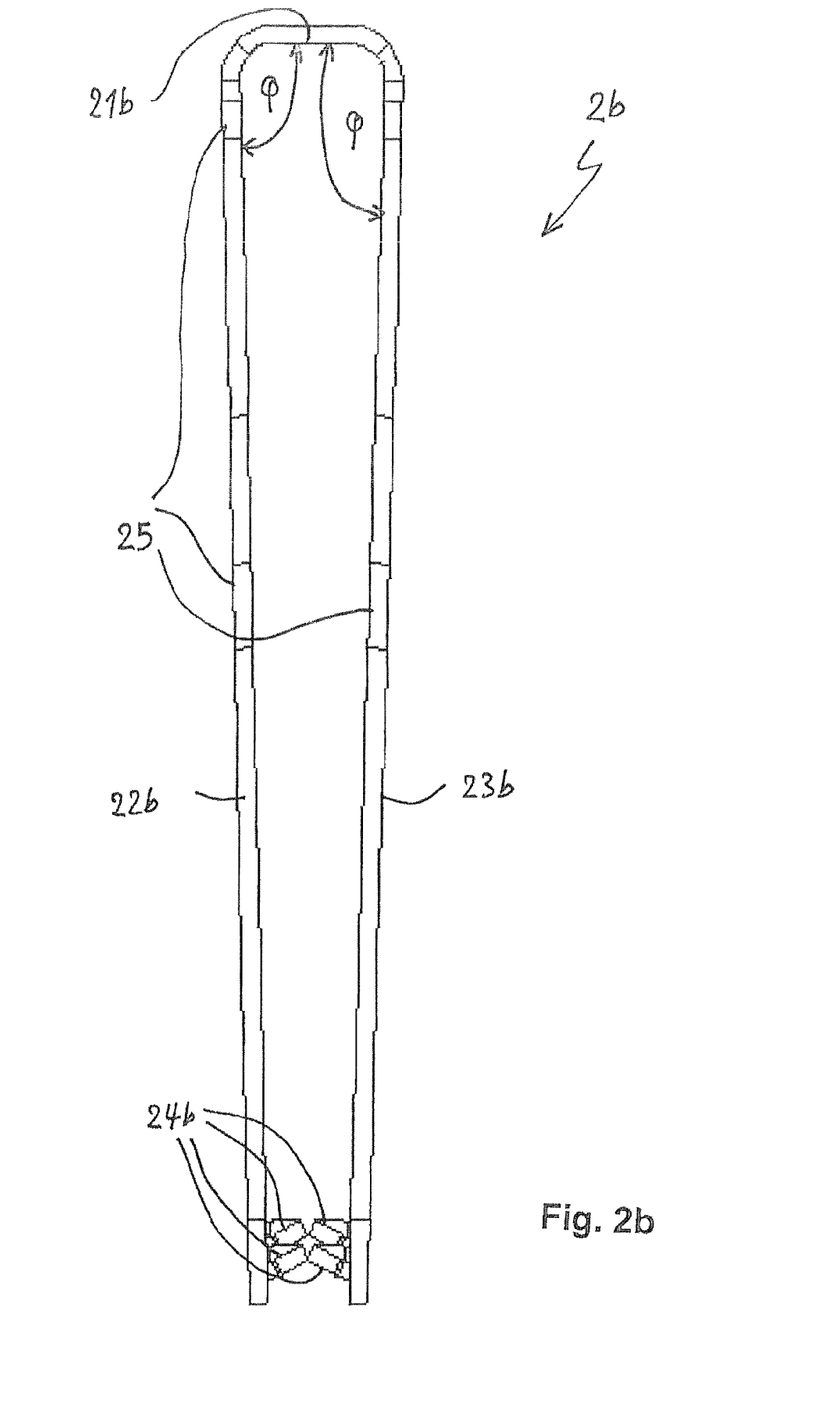
FIG. 2b depicts the implant of FIG. 2a with a substantially flat back section.

FIG. 2b shows that implant 2b, in the implanted state, bears flatly against the free lower edge of the septum.

Figure 2C:
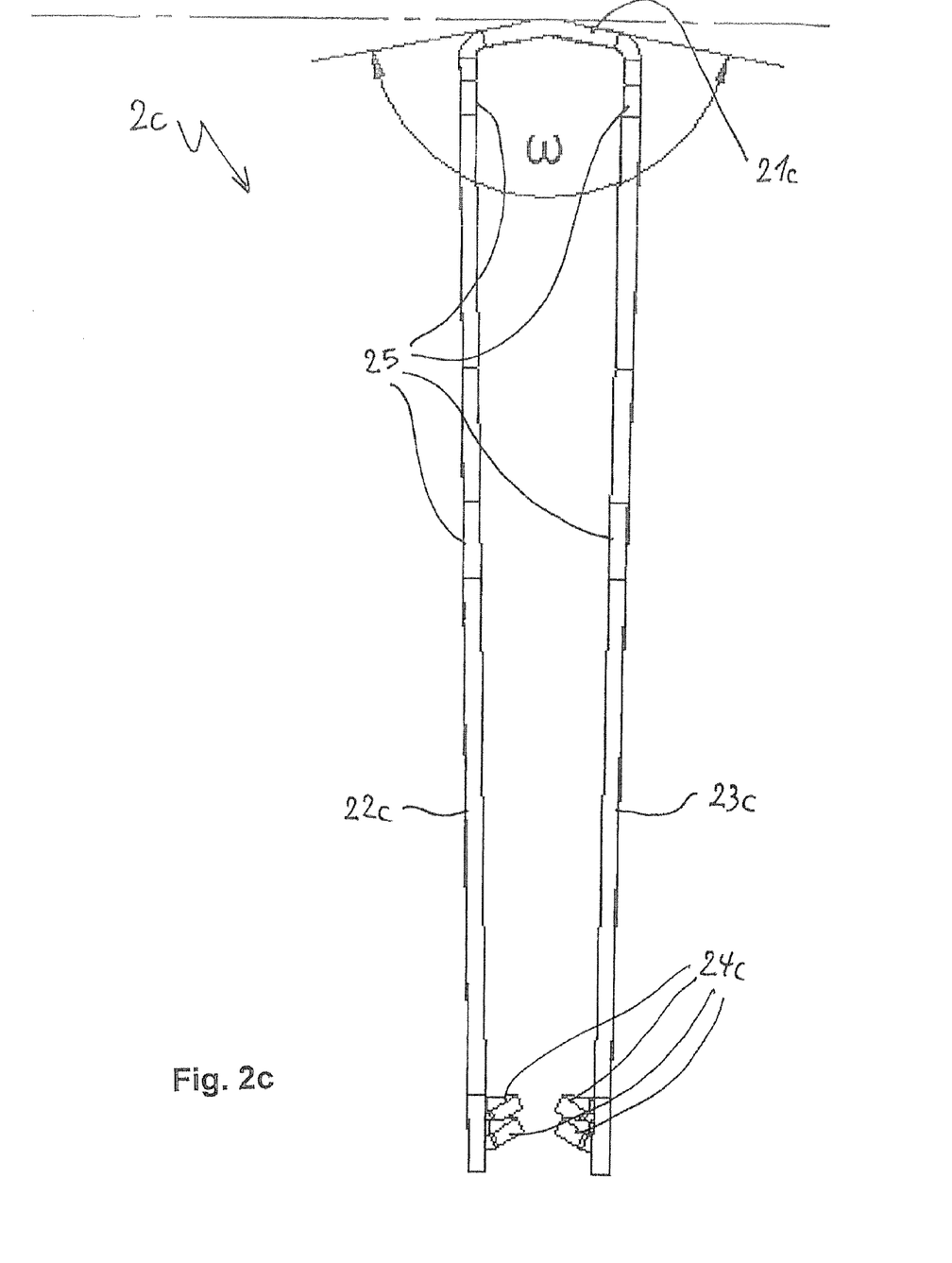
FIG. 2c depicts the implant of FIG. 2b with a roof-like back section angled at a splaying angle ω.

FIG. 2c shows that implant 2c, which is angled with respect to an "imaginary" horizontal plane at a splaying angle ω>100°, preferably ω>160°, and, in the implanted state, wraps around the free lower edge of the septum in a roof-shaped manner.

Depending on the actual configuration of the septum that is found in the particular patient, an optimally adapted geometry of the implant can be selected in an individualized manner.

As shown in FIGS. 2a to 2c, 3a to 3d and 4a, spikes 24a; 24b; 24c; 34a; 44 can be incorporated into the side sections 22a, 23a; 22b, 23b; 22c, 23c; 32a, 33a; 32b, 33b; 42a, 43a. In the implanted state of the implant 2a; 2b; 2c; 3a; 3b; 4a, the spikes dig into the septum cartilage and thereby provide a particularly secure hold.

In each of the embodiments shown in the drawings, the implant 1a; 1b; 1c; 1d; 1e; 2a; 2b; 2c; 3a; 3b; 4a comprises perforations 15; 25; 35; 45. The perforations are provided at the side sections 12a, 13a; 12b, 13b; 12c, 13c; 12d, 13d; 12e, 13e; 22a, 23a; 22b, 23b; 22c, 23c; 32a, 33a; 32b, 33b; 42a, 43a and, at the central back section of the implant located therebetween (although not depicted separately in the drawings).

Preferably, the perforations 15; 25; 35; 45 are designed as circular holes or elongated holes (as shown). The perforations help to reduce the weight of the implant and reduce the portion of exogenous material in a patient's body to the greatest extent possible. The perforations 15; 25; 35; 45 also promote the fusion of the implant with the tissue.

The implant 1a; 1b; 1c; 1d; 1e; 2a; 2b; 2c; 3a; 3b is surgically introduced into the nose by means of so-called "open rhinoplasty" and, is fastened to the cartilage of the septum S by means of suturing. A plurality of individual sutures are applied through the perforations 15; 25; 35; 45 and the septum S and are fixed.

Figure 4A:
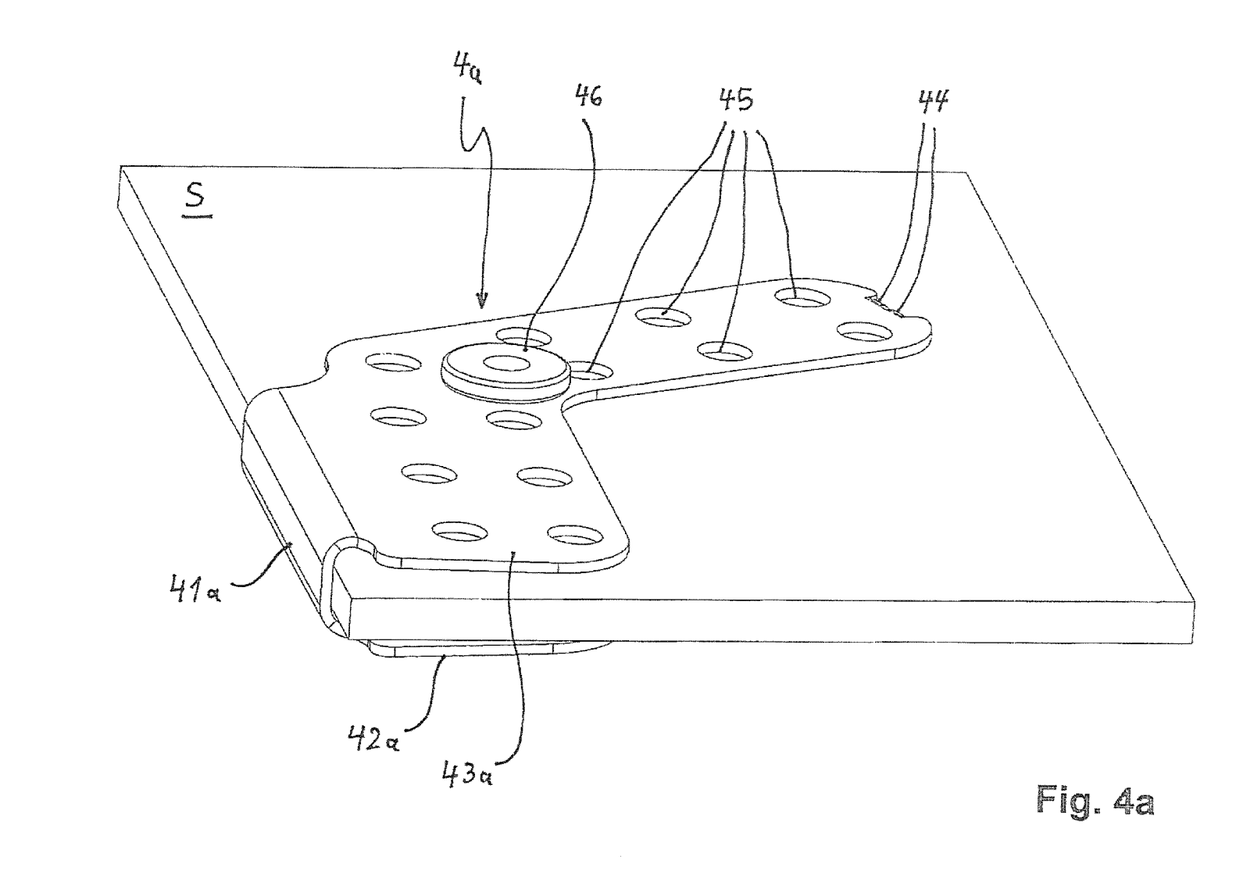
FIG. 4a presents a schematic perspective view of an implant comprising a connecting element that extends through the septum cartilage, the connecting element as shown comprising a rivet and interconnects the two side sections in the implanted state.
Figure 4B:
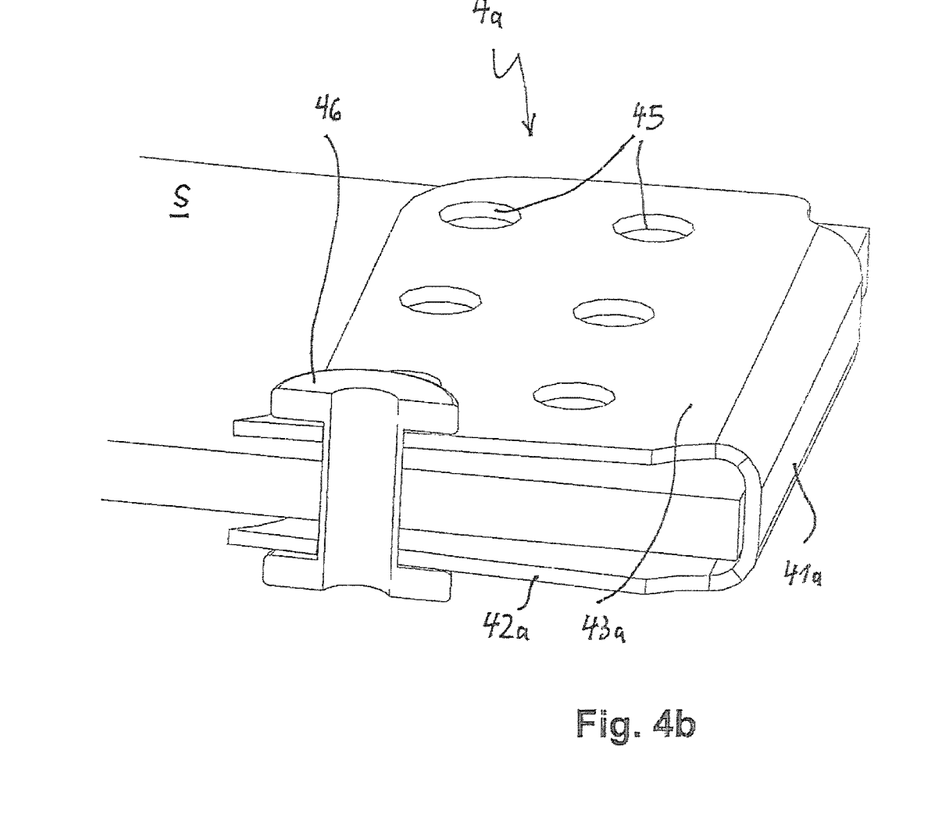
FIG. 4b depicts the implant of FIG. 4a with a sectional drawing of the implant and the septum in the region of the rivet-type connecting element.
Figure 4C:
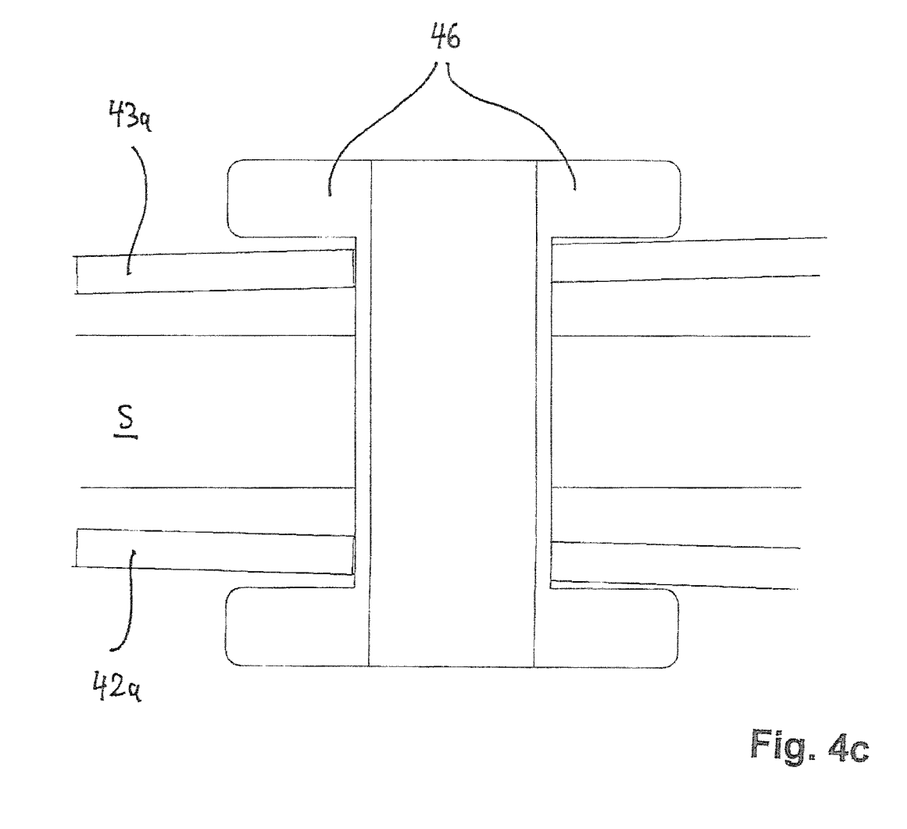
FIG. 4c presents an enlarged schematic sectional drawing of the two side sections of the FIG. 4a embodiment depicted with the septum and connecting element located therebetween.

Alternatively (or additionally), in order to fasten the implant 4a (as depicted schematically in FIGS. 4a to 4c) in the implanted state of the implant 4a, a connecting element 46 is provided. The connecting element 46 extends through the entire septum S and interconnects the two side sections 42a, 43a, which are diametrically opposed with respect to the septum S. The connecting element is preferably formed as a rivet element made of metal, in particular a titanium alloy, and provides the implant 4a with a permanent hold on the septum S.

The implant 1a; 1b; 1c; 1d; 1e; 2a; 2b; 2c; 3a; 3b; 4a is made entirely or partially of metal, in particular of titanium, a titanium alloy or stainless steel and/or a material having a memory effect and/or superelastic properties (preferably Nitinol). The implant preferably comprises a biocompatible coating.

The implant 1a; 1b; 1c; 1d; 1e; 2a; 2b; 2c; 3a; 3b; 4a is manufactured using laser technology or injection molding according to the micro injection-molding (MIM) process.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A rhinological implant for straightening a nasal septum (S) is configured to be fastened on both sides of the septum (S), separating left and right sides of a nasal cavity of a human nose, on an outer surface of the septum (S), in the left and the right sides of the nasal cavity, and is configured so that before implantation, the implant is folded up from an initially flat blank into an implantable three-dimensional shape, the implant comprising:
   a central back section that is flat or curved upwardly from a horizontal plane, angled at a splaying angle ($\omega$)>100° or has a shape of a barrel having a radius of curvature (r)≥0.5 mm from the horizontal plane, wherein in an implanted state the central back section wraps around a free lower edge of the septum, and
   two side sections provided on either side of the central back section that extend symmetrically with respect to the central back section, and are angled upwardly at an angle ($\varphi$) of approximately 90° relative to the central back section, wherein the two side sections are configured to bear via the entire surface against two diametrically opposed outer surfaces of the septum (S) in the implanted state wherein segments of a network structure are incorporated into the side sections.

2. The implant according to claim 1, wherein the two side sections have a first subsection, which directly adjoins the central back section and extends substantially parallel to the central back section, wherein each of the two side sections has a second subsection toward side section free ends, and wherein the second subsections adjoin the respective first subsection and extend at an angle relative the first subsection.

3. The implant according to claim 2, configured with an angular contour, wherein the angular contour is a V-shaped contour or a boomerang-shaped contour.

4. The implant according to claim 1, wherein corners of the side sections are rounded.

5. The implant according to claim 1, wherein one or more spikes are incorporated into the side sections.

6. The implant according to claim 1, further comprising perforations.

7. The implant according to claim 6, wherein the perforations are provided on the side sections and on the back section of the implant located between the side sections.

8. The implant according to claim 1, further comprising a connecting element which, in the implanted state of the implant extends through the entire septum (S) and interconnects the two side sections, wherein the side sections are diametrically opposed with respect to the septum (S).

9. The implant according to claim 1, formed entirely or partially of metal.

10. The implant according to claim 1, formed entirely or partially of a substance having a memory effect, superelastic properties or both.

11. The implant according to claim 1, further comprising a biocompatible coating.

12. The implant according to claim 1, formed using laser technology.

13. The implant according to claim 1, formed via injection molding according to a micro injection-molding (MIM) process.

14. The implant according to claim 1, wherein the central back section is angled at a splaying angle ($\omega$)>160°.

15. The implant according to claim 6, wherein the perforations are formed as circular holes or elongated holes.

16. The implant according to claim 8, wherein the connecting element is a rivet element.

17. The implant according to claim 9, wherein the metal is selected from the group consisting of titanium, a titanium alloy, stainless steel and a combination.

18. The implant according to claim 10, wherein the substance is nitinol.

19. A rhinological implant for straightening a nasal septum (S) is configured to be fastened on both sides of the septum (S), separating left and right sides of a nasal cavity of a human nose, on an outer surface of the septum (S), in the left and the right sides of the nasal cavity, and is configured so that before implantation, the implant is folded up from an initially flat blank into an implantable three-dimensional shape, the implant comprising:

a central back section that is flat or curved upwardly from a horizontal plane, angled at a splaying angle $(\omega)>100°$ or has a shape of a barrel having a radius of curvature $(r)\geq 0.5$ mm from the horizontal plane, wherein the back section is formed of segments of a network structure and is configured to wrap around a free lower edge of the septum in an implanted state; and two side sections provided on either side of the central back section that extend symmetrically with respect to the central back section and are angled upwardly at an angle $((p)$ of approximately 90° relative to the central back section;

wherein the two side sections are configured to bear via the entire surface against two diametrically opposed outer surfaces of the septum (S) in the implanted state.

* * * * *